(12) United States Patent
Döbelin et al.

(10) Patent No.: US 9,611,173 B2
(45) Date of Patent: Apr. 4, 2017

(54) CALCIUM PHOSPHATE CEMENT COMPOSITION

(71) Applicant: MATHYS AG BETTLACH, Bettlach (CH)

(72) Inventors: Nicola Döbelin, Solothurn (CH); Hanna Tiainen, Oslo (NO); Marc Bohner, Grenchen (CH)

(73) Assignee: Mathys AG Bettlach, Bettlach (CH)

( * ) Notice: Subject to any disclaimer, the term of this patent is extended or adjusted under 35 U.S.C. 154(b) by 0 days.

(21) Appl. No.: 14/785,818

(22) PCT Filed: Apr. 22, 2013

(86) PCT No.: PCT/CH2013/000068
§ 371 (c)(1),
(2) Date: Oct. 20, 2015

(87) PCT Pub. No.: WO2014/172794
PCT Pub. Date: Oct. 30, 2014

(65) Prior Publication Data
US 2016/0075599 A1   Mar. 17, 2016

(51) Int. Cl.
C04B 12/02 (2006.01)
A61L 24/02 (2006.01)
B65D 25/08 (2006.01)
B65D 81/32 (2006.01)
C04B 40/06 (2006.01)

(52) U.S. Cl.
CPC ............ *C04B 12/025* (2013.01); *A61L 24/02* (2013.01); *B65D 25/08* (2013.01); *B65D 81/32* (2013.01); *C04B 40/065* (2013.01); *A61L 2430/02* (2013.01)

(58) Field of Classification Search
CPC .................................................. C04B 12/025
See application file for complete search history.

(56) References Cited

U.S. PATENT DOCUMENTS

| 2005/0186353 A1* | 8/2005 | Lin ...................... C04B 35/447 427/430.1 |
| 2011/0152195 A1* | 6/2011 | O'Mahony ........... A61L 24/001 514/16.7 |

FOREIGN PATENT DOCUMENTS

| WO | 03/041753 A1 | 5/2003 |
| WO | 2007/056872 A1 | 5/2007 |

\* cited by examiner

*Primary Examiner* — Paul Marcantoni
(74) *Attorney, Agent, or Firm* — Rankin, Hill & Clark, LLP

(57) ABSTRACT

A calcium phosphate cement composition that includes the following two components: A) one or several calcium phosphate powders suspended in an aqueous solution including inhibitor cations inhibiting a reaction of the calcium phosphate powders with water, the inhibitor cations being selected from $Mg^{2+}$, $Sr^{2+}$ and $Ba^{2+}$ at a concentration greater than 0.01 M; and B) an aqueous solution including $Ca^{2+}$ cations at a concentration greater than 0.1 M. This calcium phosphate cement compositions can be safely stored for years yet still retain its full reactivity when mixed.

30 Claims, 10 Drawing Sheets

CALCIUM PHOSPHATE CEMENT COMPOSITION

BACKGROUND OF THE INVENTION

1. Field of the Invention

The invention relates to a calcium phosphate cement composition that comprises two components and to a dual chamber device having a separator between the two chambers that can be removed to allow for mixing of the composition.

2. Description of the Related Art

Most commercial cements are in the form of two components: a solid component (i.e. a powder or powder mixture) and a liquid component. These cements have a good shelf-life stability provided the two components are kept separate. To initiate the setting/hardening reaction, the two components (solid+liquid) must be mixed just prior to the application. Indeed, as soon as the liquid contacts the solid, the setting reaction starts. Generally, the paste obtained by mixing the liquid with the solid component must be transferred from the mixing container into an injection system. In other words, handling is not very good (the powder and the liquid need to be mechanically mixed; the resulting paste must be transferred into an injection system; the calcium phosphate cement (CPC) paste needs to be injected within a short time after powder-liquid mixing).

From WO 03/041753 (Lemaitre) a CPC is known based on the mixture of two calcium phosphate pastes. The main advantage of this prior art cement relies in the possibility to mix the two pastes by injection through a static mixer. Provided the two pastes can react together (e.g. via an acid-base reaction), it is possible to design a CPC that is mixed during injection. In other words, there is no need to mix a powder with a liquid or to transfer the resulting paste into an injection system. Lemaitre disclosed three examples of CPC formulations. In example 1, the end product of the reaction was a so-called "brushite" (dicalcium phosphate dihydrate; $CaHPO_4.2H_2O$). Both components were stable during years. In the second example, a paste consisting mainly of tetracalcium phosphate (TetCP; $Ca_4(PO_4)_2O$) was mixed with a paste consisting mainly of dicalcium phosphate ($CaHPO_4$). Whereas the second paste was most likely stable during years, there were no scientific data showing that the first phase would remain stable during years. Considering the very large reactivity of TetCP the paste stability is limited to a few minutes. The third example is devoted to CPCs made of alpha-tricalcium phosphate (alpha-TCP). Contrary to the statement made in Lemaitre, it was not possible to reproduce the claimed results: α-TCP reacted within a few hours/days with water to form calcium-deficient hydroxyapatite (CDHA).

What is therefore needed are calcium phosphate compositions which can be safely stored for years and still retain their full reactivity when mixed.

In other words, the first paste ("Component A") consisting of a mixture of reactive calcium phosphate powder and water must contain a reaction inhibitor to prevent the transformation of the reactive calcium phosphate powder into an apatite phase. Furthermore, the second paste ("Component B") must contain a substance able to activate the reaction of the reactive calcium phosphate powder present in the first paste, a so-called "activator".

The invention solves this task with a calcium phosphate cement composition comprising two components and with a dual-chamber device having a separator between the two chambers that can be removed to allow for mixing of the composition.

Component A preferably comprises a reactive calcium phosphate powder (tetracalcium phosphate (TetCP), $Ca_4(PO_4)_2O$, α-tricalcium phosphate (α-TCP), amorphous calcium phosphate (ACP), $Ca_3(PO_4)_2.nH_2O$, water, and a reaction inhibitor. The reaction inhibitor can either inhibit the dissolution of the reactive calcium phosphate powder, or preferably the precipitation of an apatite. Here, the term "apatite" is used to designate various compounds or mixtures thereof such as hydroxyapatite (HA); $Ca_5(PO_4)_3OH$), calcium-deficient hydroxyapatite (CDHA); $2Ca_9(HPO_4)(PO_4)_5OH$), carbonated apatite, fluorapatite, chlorapatite, oxyapatite, or ion-substituted apatite. These compounds can have slightly different compositions but all have the same crystallographic structure. As a result, all inhibitors of e.g. hydroxyapatite can be used to inhibit other apatite forms, such as e.g. carbonated apatite. Typical substances that can be used include anions like carboxylated compounds (e.g. citrate, polyacrylates), pyrophosphates and bisphosphonates, as well as cations like Mg or Zn. More complex molecules like peptides and proteins can also be used. All these substances can be quoted to be "inhibitors". However, it has surprisingly become apparent that only $Mg^{2+}$, $Sr^{2+}$ or $Ba^{2\pm}$ cations can be considered to be adequate inhibitors for the present invention.

The inhibitor concentration is important. As the action of inhibitors is related to their adsorption on active sites (e.g. dislocations) of calcium phosphate particles, the inhibitor concentration must be large enough to block all active sites: a concentration superior to 0.01M of the inhibitor cations is required.

Contrary to amorphous calcium phosphate, α-TCP is produced using a high-temperature thermal treatment followed by milling. During the milling step, part of the powder becomes amorphous. This amorphous part is highly reactive. It has been possible to show that this amorphous part could be removed by a thermal treatment in the range of 400 to 700° C. Therefore, α-TCP powder is preferably calcined to keep a high calcium phosphate-water paste stability during shelf-life.

Component B must contain a substance able to anneal the effect of the inhibitor present in component A. Throughout the patent it is called the "activator". As the action of inhibitors is related to their adsorption on active sites of calcium phosphate particles, the activator must be able to displace the inhibitor without itself inhibiting the CPC reaction. Surprisingly observations showed that $Ca^{2+}$ cations can displace $Mg^{2+}$, $Sr^{2+}$ or $Ba^{2+}$ cations and activate the reaction. The effect is dependent on the concentration, which has to be at least 0.01 M and preferably there should be at least 2 times, preferably 5 times more $Ca^{2+}$ cations than $Mg^{2+}$, $Sr^{2+}$ or $Ba^{2+}$ cations.

The advantage of the calcium phosphate cement composition according to the invention is its prolonged storage capability.

Further advantageous embodiments of the invention can be commented as follows:

Particularly good results were obtained when the inhibitor cations were selected from $Mg^{2+}$ only or from $Sr^{2+}$ only.

The ratio of component A to component B is preferably such that upon mixing of the two components the molar ratio of $Ca^{2+}$ ions/inhibitor cations in the mixture is superior to 2, preferably superior to 5.

The calcium phosphate powder to be used with the calcium phosphate cement composition is preferably alpha-tricalcium phosphate or amorphous calcium phosphate (ACP).

Purposefully the a-tricalcium phosphate powder is obtained by calcination at a temperature in the range of 400° C. to 700° C. for at least 10 minutes. This treatment leads to a reduction of the a-tricalcium phosphate powder reactivity with water in the absence of an inhibitor.

The concentration of the inhibitor cations in component A is preferably equal to or larger than 0.05 M, preferably larger than 0.1 M.

Purposefully component B comprises highly soluble calcium salts with a solubility superior to 0.5 M, preferably superior to 1.0 M.

In special embodiments component B comprises one or more of the following calcium salts:

calcium chloride (anhydrous: $CaCl_2$, monohydrate: $CaCl_2.H_2O$, dihydrate: $CaCl_2.2H_2O$, or hexahydrate: $CaCl_2.6H_2O$), dicalcium phosphate dihydrate ($CaHPO_4.2H_2O$; DCPD), calcium sulphate dihydrate ($CaSO_4.2H_2O$; CSD), calcium sulphate hemihydrate ($CaSO_4.\frac{1}{2}H_2O$; CSH), calcium sulphate ($CaSO_4$), calcium nitrate, calcium acetate (anhydrous: $Ca(C_2H_3O_2)_2$, monohydrate: $Ca(C_2H_3O_2)_2.H_2O$, or dihydrate $Ca(C_2H_3O_2)_2.2H_2O$), calcium citrate ($Ca_3(C_6H_5O_7).4H_2O$), calcium fumarate ($CaC_4H_2O_4.3H_2O$), calcium glycerophosphate ($CaC_3H_5(OH_2)PO_4$), calcium lactate ($Ca(C_3H_5O_3)_2.5H_2O$), calcium malate (dl-malate: $CaC_4H_4O_5.3H_2O$, l-malate: $CaC_4H_4O_5.2H_2O$, or malate dihydrogen: $Ca(HC_4H_4O_5)_2.6H_2O$), calcium maleate ($CaC_4H_2O_4.H_2O$), calcium malonate ($CaC_3H_2O_4.4H_2O$), calcium oxalate ($CaC_2O_4$), calcium oxalate hydrate ($CaC_2O_4.H_2O$), calcium salicylate. ($Ca(C_7H_5O_3)_2.2H_2O$), calcium succinate ($CaC_4H_6O_4.3H_2O$), calcium tartrate (d-tartrate: $CaC_4H_4O_6.4H_2O$; dl-tartrate: $CaC_4H_4O_6.4H_2O$; mesotartrate: $CaC_4H_4O_6.3H_2O$), and calcium valerate ($Ca(C_5H_9O_2)_2$).

Preferably the volume ratio of the two components A/B is equal to or larger than 4 and is preferably lower than 12.

In a further embodiment the concentration of $Ca^{2+}$ ions in component B is superior to 0.5 M.

In a further embodiment component B comprises a calcium phosphate powder, in particular an apatite, preferably a pure hydroxyapatite, an ion-substituted hydroxyapatite such as Si- or Sr-substituted apatite, or a Ca-deficient hydroxyapatite (CDHA). These compounds prevent phase separation (solid-liquid) during injection because when the particles are very small, it is more difficult for the liquid to flow between the particles to reach phase separation.

In a special embodiment the quantity of calcium phosphate powder in component B is equal to or larger than 0.4 g/mL, preferably larger than 1.0 g/mL In a further embodiment the particles of the calcium phosphate powder are nanocrystals, preferably with a mean diameter of 100 nm. The resulting water-nanocrystals pastes have exhibited surprisingly good rheological properties, being easily injectable and cohesive, i.e. the paste does not easily disintegrate when injected into a liquid, such as blood.

In a further embodiment component A or B or both comprise a small amount of water soluble polymer. This additive generates a gel with a markedly increased liquid viscosity which prevents phase separation (solid-liquid) during injection. The polymer can be chosen from the group of: (i) hyaluronan, preferably sodium hyaluronate or hyaluronic acid); (ii) chondroitin sulphate; (iii) cellulose derivatives, preferably hydroxypropylmethyl cellulose or methylcellulose; (iv) polyvinylpyrrolidone; (v) N-methyl-2-pyrrolydone or (vi) dimethylsiloxane; (vii) alginate, (viii) chitosan, (ix) gelatine, (x) collagen. The amount of polymer is purposefully at least 0.1 weight %, preferably at least 0.3 weight %. The amount of polymer purposefully is at most 3.0 weight %, preferably at most 2.0 weight %.

The calcium phosphate cement can further comprise a radiopacifier, chosen from the following groups: (i) iodine based solutions, preferably iohexol, iodixanol and ioversol; (ii) metallic powders, preferably Ta; or (iii) ceramics, preferably tungsten carbide, bismuth oxide or zirconium oxide.

The calcium phosphate-to-liquid weight ratio upon mixing of components A and B is preferably equal to or larger than 2.

Purposefully the pH of component B is equal to or lower than 6, preferably lower than 5. The pH of component B may be adjusted using a weak acid, preferably using acetic acid, formic acid, lactic acid, citric acid, and propionic acid. The concentration of the weak acid in component B is purposefully equal to or larger than 0.1 M, preferably larger than 0.2 M.

The pH of component A is purposefully superior to 8, preferably superior to 9.

In a special embodiment the alpha-tricalcium phosphate has a purity of more than 80%, preferably of more than 90%. The alpha-tricalcium phosphate is preferably contaminated with apatite.

In a further embodiment the alpha-tricalcium phosphate has a specific surface area (SSA) larger than 0.5 $m^2/g$, preferably larger than 2.0 $m^2/g$.

The dual chamber device according to the invention has two separate chambers $C_A$ and $C_B$ the content of which can be mixed upon removing the separation between the two chambers and wherein chamber $C_A$ contains component A and chamber $C_B$ contains component B of the calcium phosphate cement composition according to the invention. Preferably the volume ratio A/B of component A to component B in the dual chamber device is in the range of 4:1 and 12:1.

A BRIEF DESCRIPTION OF THE DRAWINGS

Several embodiments of the invention will be described in the following by way of example and with reference to the accompanying drawings in which.

Figure 2:
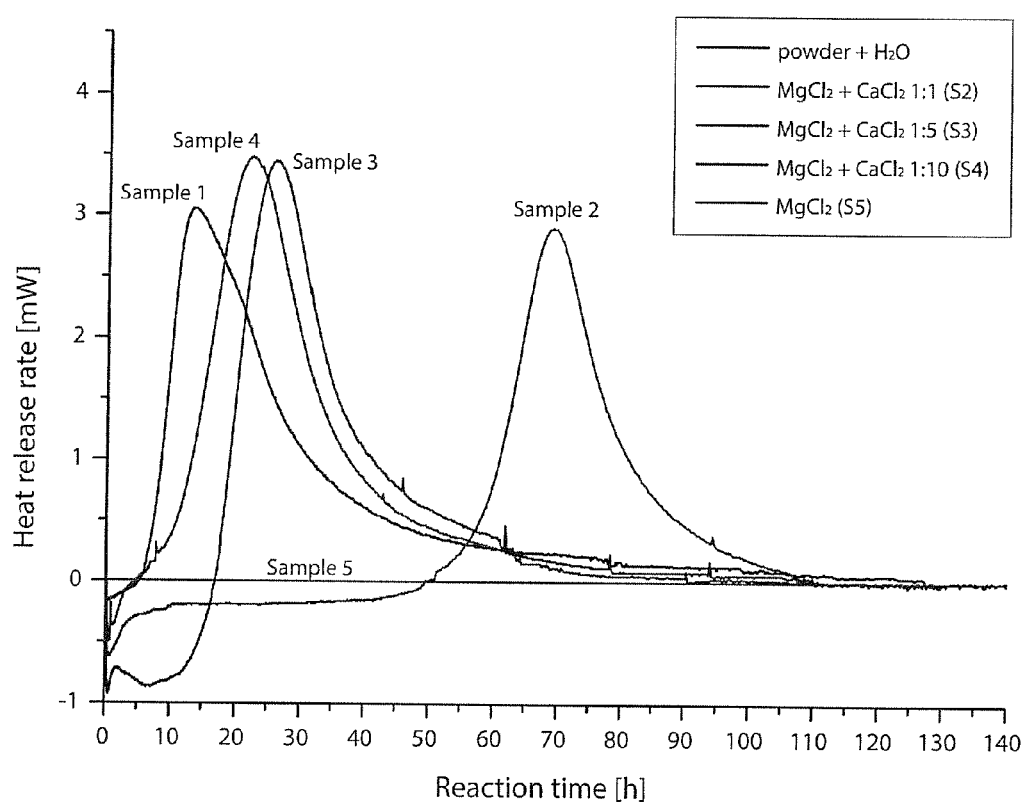
FIG. 2 is a graph illustrating typical heat release curves obtained by isothermal calorimetry with 2 g of α-TCP particles in 0.8 ml 0.1M $MgCl_2$ solution when 0.2 ml of aqueous solution containing various concentrations of $CaCl_2$ are added.
Figure 4:
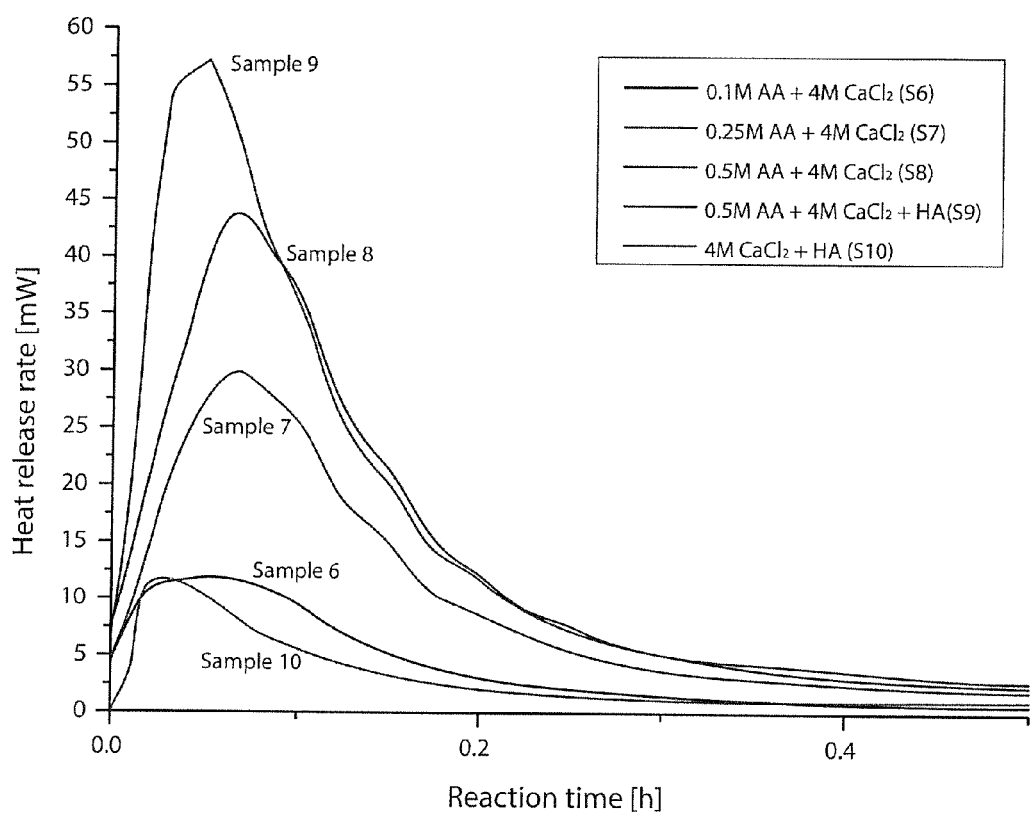
Figure 5:
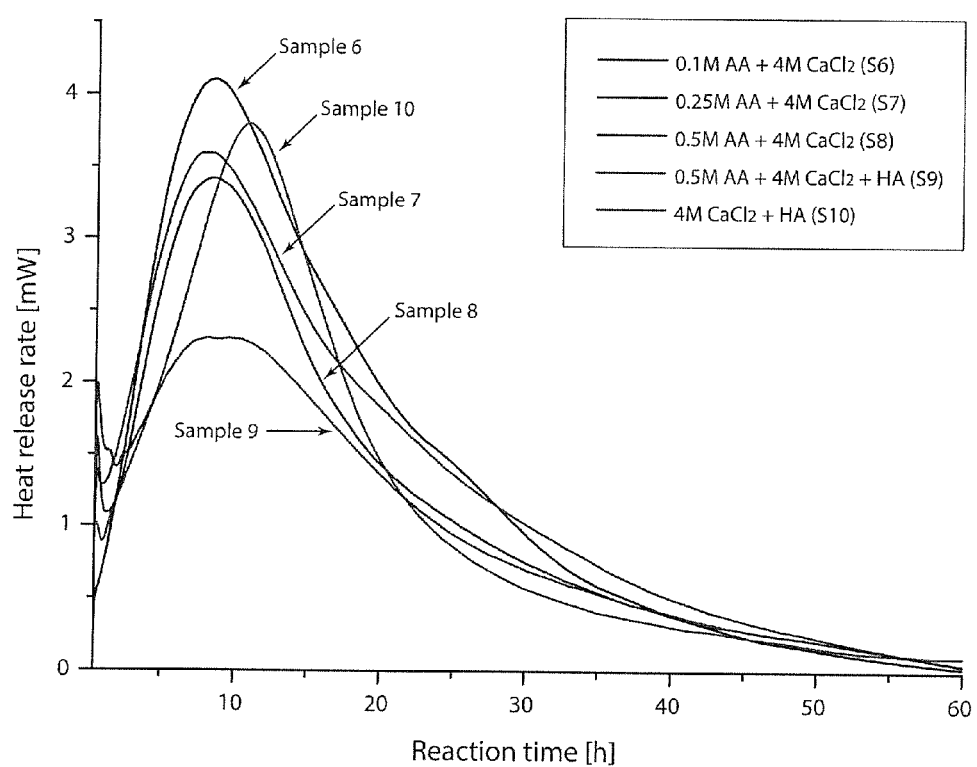
Figure 6:
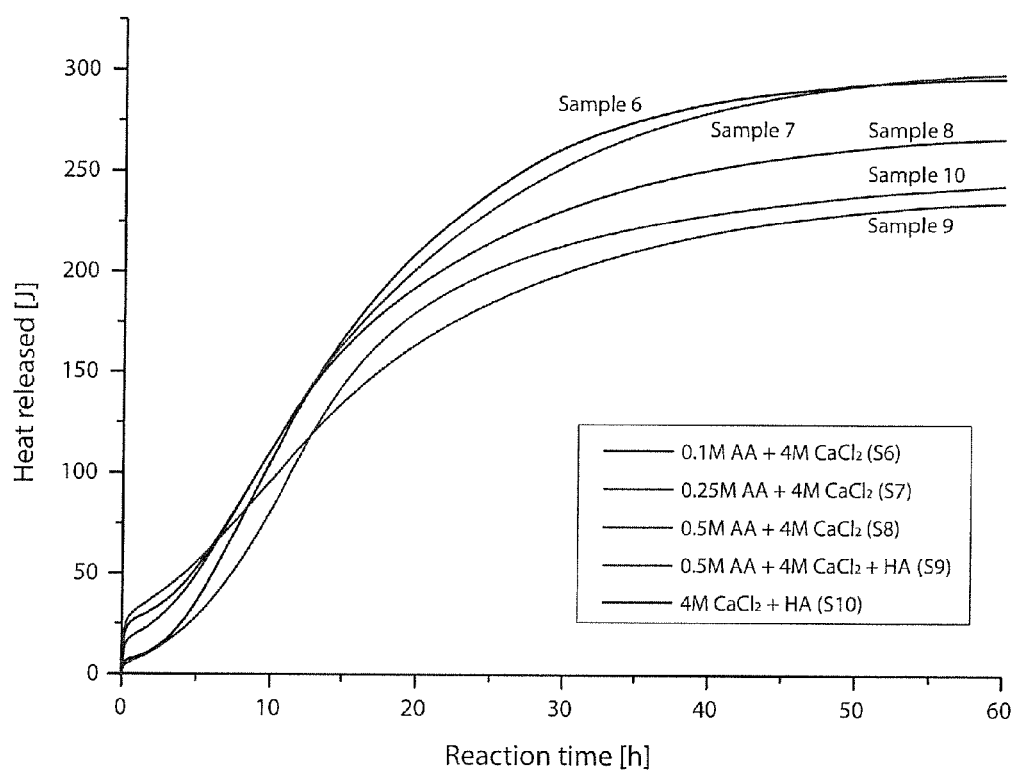
Figure 7:
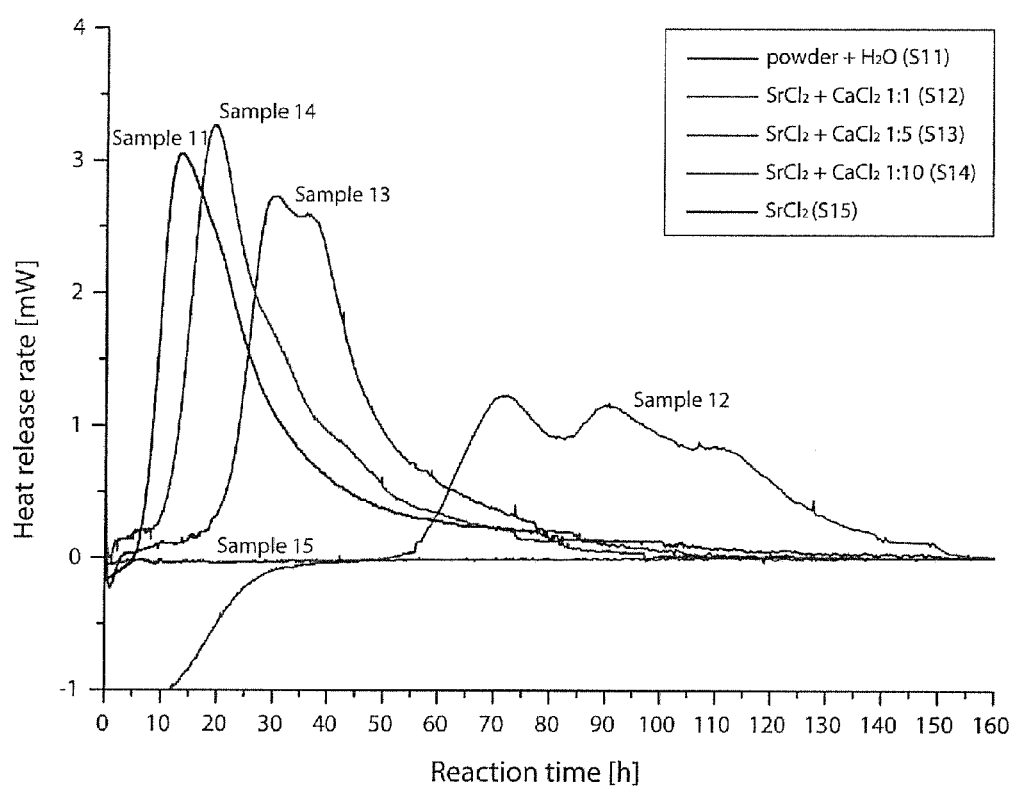
Figure 8:
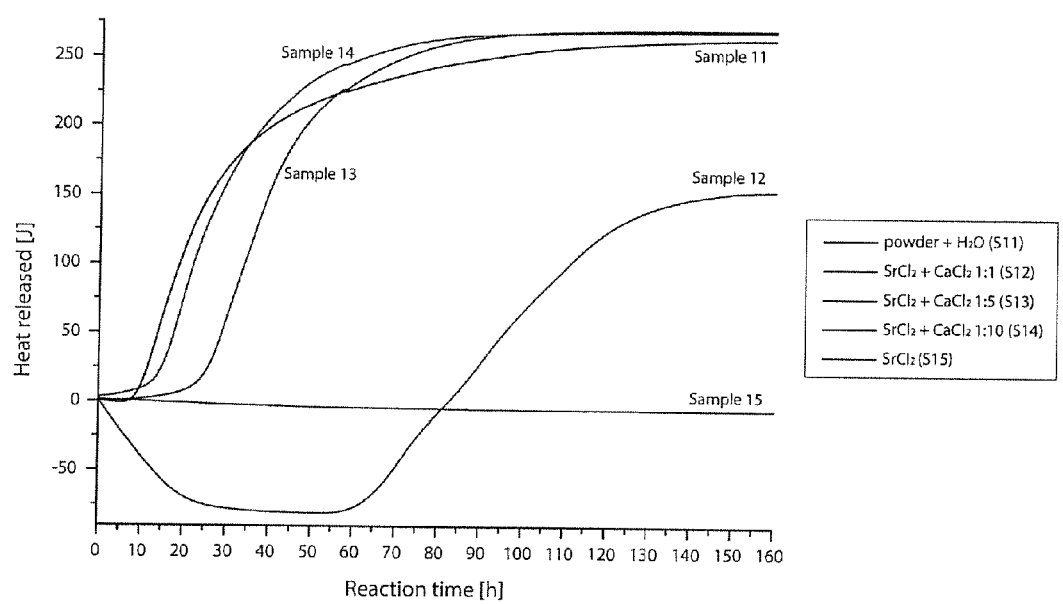
Figure 9:
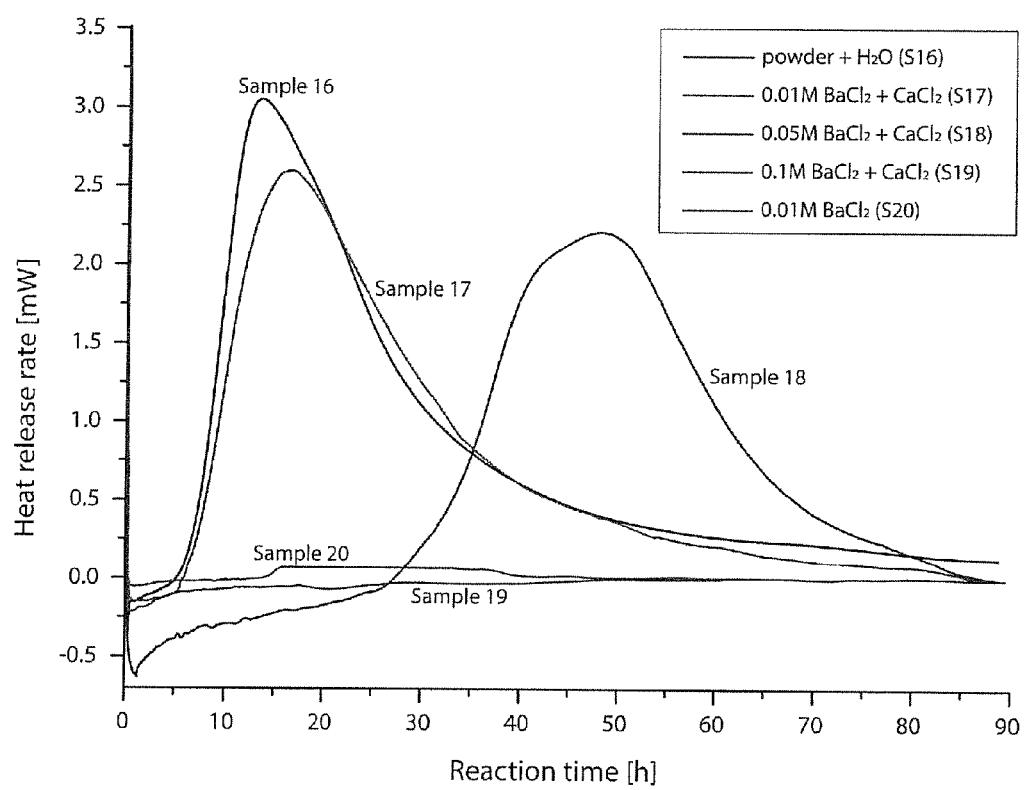
Figure 10:
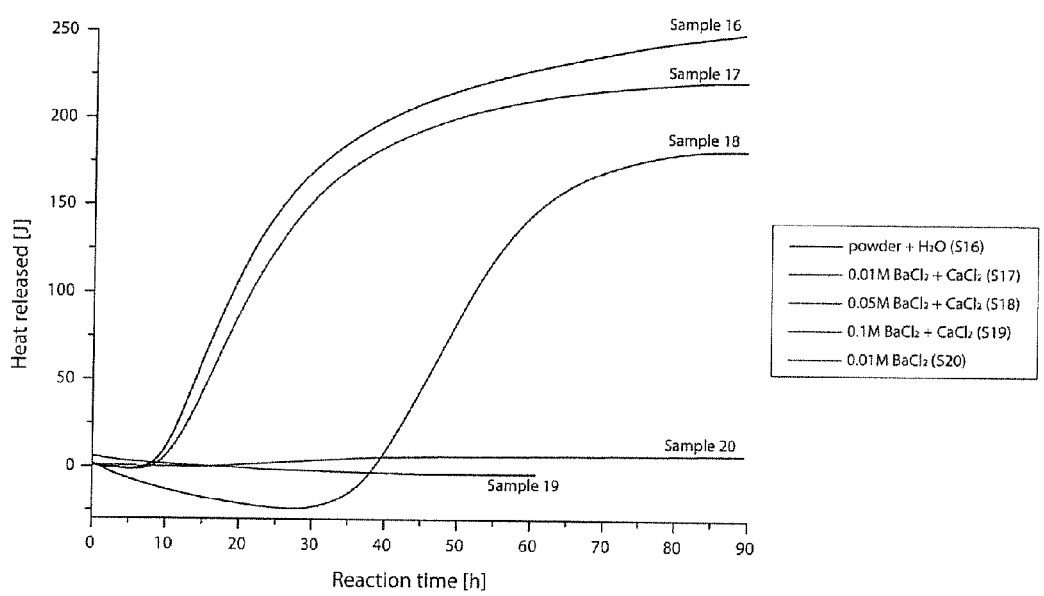

FIG. 4 is a graph illustrating typical heat release curves obtained by isothermal calorimetry during the first 30 minutes of the experiment with 2 g of α-TCP particles in 0.8 ml 0.1M $MgCl_2$ solution when 0.2 ml of aqueous $CaCl_2$ solution containing various concentrations of acetic acid and/or HA seed crystal are added;

FIG. 5 is a graph illustrating typical heat release curves obtained by isothermal calorimetry after the first 30 minutes of the experiment with 2 g of α-TCP particles in 0.8 ml 0.1M MgCl$_2$ solution when 0.2 ml of aqueous CaCl$_2$ solution containing various concentrations of acetic acid and/or HA seed crystal are added;

FIG. 6 is a graph illustrating typical heat release curves of the cumulated total heat obtained from the release curves in FIGS. 4 and 5;

FIG. 7 is a graph illustrating typical heat release curves obtained by isothermal calorimetry with 2 g of α-TCP particles in 0.8 ml 0.1M SrCl$_2$ solution when 0.2 ml of aqueous solution containing various concentrations of CaCl$_2$ are added;

FIG. 8 is a graph illustrating typical heat release curves of the cumulated total heat obtained from the release curves in FIG. 2;

FIG. 9 is a graph illustrating typical heat release curves obtained by isothermal calorimetry with 2 g of α-TCP particles in 0.8 ml BaCl$_2$ solution when 0.2 ml of aqueous solution containing various concentrations of CaCl$_2$ are added; and FIG. 10 is a graph illustrating typical heat release curves of the cumulated total heat obtained from the release curves in FIG. 9.

The following examples clarify the invention further in more detail.

EXAMPLE 1

This example describes the use of a calcium phosphate cement consisting of two components: (A) a mixture of 6.0 g of α-tricalcium phosphate powder (α-TCP; Ca$_3$(PO$_4$)$_2$; SSA value: 0.6 m$^2$/g; >99% purity; calcined at 500° C. for 24 h prior to being dispersed in the MgCl$_2$ solution) and 2.6 ml of 0.1 M magnesium chloride (MgCl$_2$) solution and (B) 0.52 ml of 5 M calcium chloride (CaCl$_2$) solution.

Although α-TCP is known to react with water to form calcium-deficient hydroxyapatite (CDHA; Ca$_9$(PO$_4$)$_5$(HPO$_4$)OH; reaction 1), this reaction does not occur in component A because of two factors i) α-TCP powder was calcined at 500° C. for 24 h prior to dispersing it in the aqueous medium. This treatment has been shown to passivate the α-TCP particles and thus results in α-TCP powder with low reactivity, and ii) the a-TCP powder is mixed with an aqueous solution containing an inhibitor for CDHA nucleation and crystal growth (=Mg$^{2+}$ ion). The combination of both these features is important for obtaining a paste that maintains its stability over several years of storage.

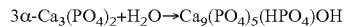

$$3\alpha\text{-Ca}_3(\text{PO}_4)_2 + \text{H}_2\text{O} \rightarrow \text{Ca}_9(\text{PO}_4)_5(\text{HPO}_4)\text{OH} \quad [1]$$

The two components A and B are stored in separate chambers of a dual-chamber syringe with 10:1 volume ratio until the eventual application of the cement. To initiate the cement reaction and hence hardening, components A and B are mixed together. Component B contains calcium ions as an activator which displaces the CDHA nucleation and crystal growth inhibitors present on the particle surface (=Mg$^{2+}$ ions), thus initiating the cement reaction in aqueous environment. The mixing of the two components can be achieved by injecting the two components through a static mixer attached to the syringe. Alternatively, the two components A and B may also be mixed with each other using other methods such as with bowl and spatula.

In order to accelerate the initiation of the setting reaction, apatite crystals may be incorporated into component B, or alternatively, the pH of component B may be adjusted to lower pH values as will be further illustrated in Example 3.

EXAMPLE 2

Several samples of calcium phosphate cement compositions according to the invention with various compositions were tested in an isothermal calorimeter at 37° C. using the parameters described in Table 1.

TABLE 1

Composition of the cement samples tested in isothermal calorimeter

| Sample | Component A | Component B |
|---|---|---|
| 1 | 2.0 g of calcined α-TCP powder | 1.0 ml demineralised H$_2$O |
| 2 | 2.0 g of calcined α-TCP powder mixed with 0.8 ml 0.1M MgCl$_2$ solution | 0.2 ml 0.4M of CaCl$_2$ solution |
| 3 | 2.0 g of calcined α-TCP powder mixed with 0.8 ml 0.1M MgCl$_2$ solution | 0.2 ml 2.0M of CaCl$_2$ solution |
| 4 | 2.0 g of calcined α-TCP powder mixed with 0.8 ml 0.1M MgCl$_2$ solution | 0.2 ml 4.0M of CaCl$_2$ solution |
| 5 | 2.0 g of calcined α-TCP powder mixed with 0.8 ml 0.1M MgCl$_2$ solution | 0.2 ml demineralised H$_2$O |

The α-TCP powder (the same as the one used in example 1) was placed in a glass vial compartment of the sealed mixing cell used for the calorimeter experiment, while the liquid component of A was placed in one of the two sealed injection compartments of the mixing cell. The other one of these liquid compartments contained component B. Immediately after placing the mixing cell thus containing both components A and B within the calorimeter, the liquid component, i.e. the MgCl$_2$ solution, of component A was injected into the α-TCP powder and the powder and liquid were mixed together to a cement paste using the mixing rod present in the mixing cell. Following a 2 h incubation time during which both components reached the temperature of 37° C. as indicated by a constant calorimetric signal, component B was injected into the mixing cell containing component A and the formed paste was mixed with the mixing rod. The calorimetric signal was measured until a constant null value was obtained, typically more than 48 h after the injection of component B.

Figure 1:
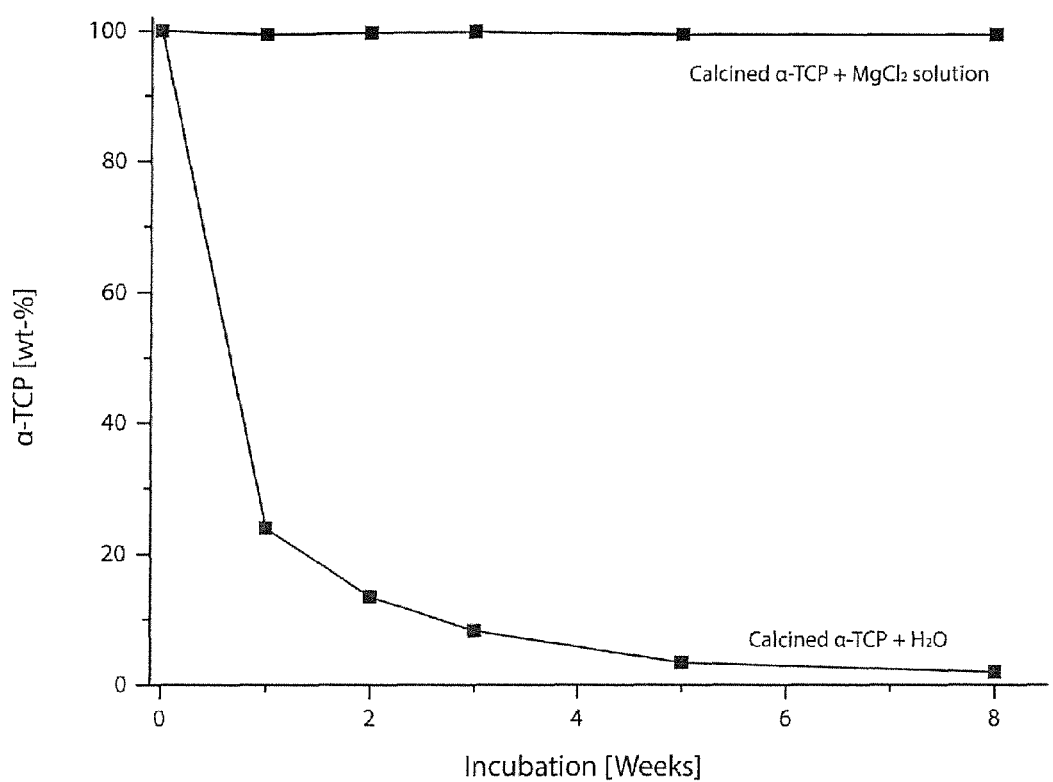
FIG. 1 is a graph illustrating the crystalline composition of the solid phase in component A following increasing storage time as analyzed by x-ray diffraction.

As shown in FIG. 1, the α-TCP paste maintains its stability in the aqueous MgCl$_2$ solution when stored at room temperature for extended periods of time. Similarly, no hydraulic cement reaction indicated by significant heat release was detected for the sample containing 0.1 M MgCl$_2$ solution with no added activator component (sample 5) in isothermal calorimetry experiments at 37° C. during a 24 days testing period, after which time the experiment was terminated. In comparison, calcined α-TCP containing no Mg$^{2+}$ ions as nucleation and grain growth inhibitors (sample 1) reacted readily in aqueous environment with the setting reaction initiating less than 10 h after exposure to water (FIG. 2).

Figure 3:
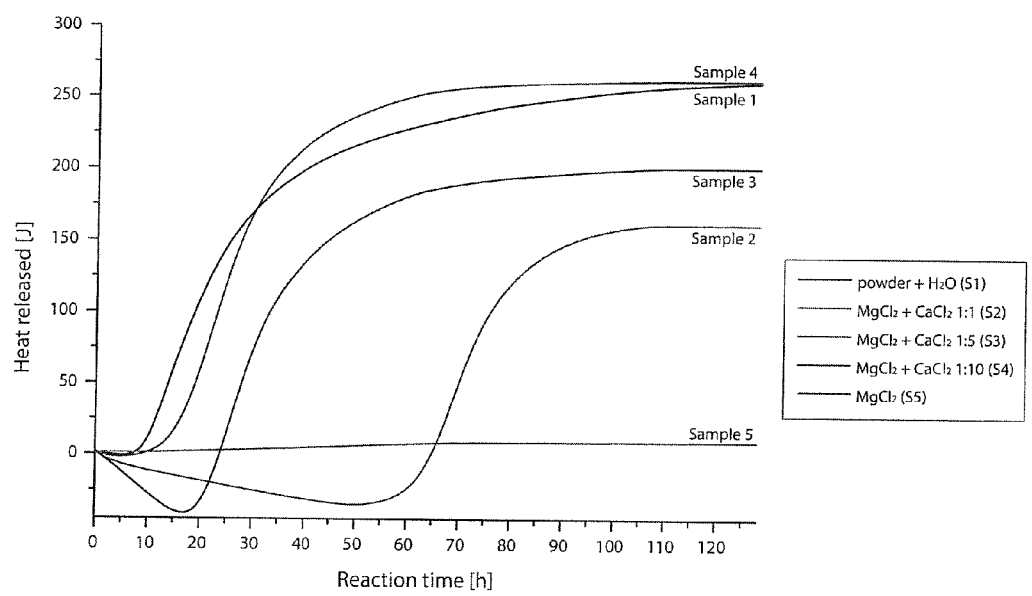
FIG. 3 is a graph illustrating typical heat release curves of the cumulated total heat obtained from the release curves in FIG. 2.

Addition of increasing amount Ca$^{2+}$ ions as activators into component B (samples 2-4) resulted in increasingly accelerated initiation of the setting reaction with the highest tested concentration resulting in a hydraulic reaction after approximately 12 h as illustrated in FIG. 2. Total amount of heat released during the setting reaction was somewhat lower at low Ca$^{2+}$-to-Mg$^{2+}$ ratios (FIG. 3). The results indicate that the Ca$^{2+}$ ions have the capacity to anneal the effect of the reaction-inhibiting Mg$^{2+}$ ions (probably by displacing them from the α-TCP particle surface) and thus initiating the cement reaction.

EXAMPLE 3

Several samples of calcium phosphate cement compositions according to the invention were tested in an isothermal calorimeter at 37° C. using the parameters described in Table 2.

TABLE 2

Composition of the cement samples tested in isothermal calorimeter

| Sample | Component A | Component B |
|---|---|---|
| 6 | 2.0 g of calcined α-TCP powder mixed with 0.8 ml 0.1M $MgCl_2$ solution | 0.2 ml of a mixture of 4M $CaCl_2$ and 0.1M acetic acid solutions |
| 7 | 2.0 g of calcined α-TCP powder mixed with 0.8 ml 0.1M $MgCl_2$ solution | 0.2 ml of a mixture of 4M $CaCl_2$ and 0.25M acetic acid solutions |
| 8 | 2.0 g of calcined α-TCP powder mixed with 0.8 ml 0.1M $MgCl_2$ solution | 0.2 ml of a mixture of 4M $CaCl_2$ and 0.5M acetic acid solutions |
| 9 | 1.8 g of calcined α-TCP powder and 0.2 g of HA mixed with 0.8 ml 0.1M $MgCl_2$ solution | 0.2 ml of a mixture of 4M $CaCl_2$ and 0.5M acetic acid solutions |
| 10 | 1.8 g of calcined α-TCP powder and 0.2 g of HA mixed with 0.8 ml 0.1M $MgCl_2$ solution | 0.2 ml 4M $CaCl_2$ solution |

The α-TCP powder (the same as the one used in example 1) was placed in a glass vial compartment of the sealed mixing cell used for the calorimeter experiment, while the liquid component of A was placed in one of the two sealed injection compartments of the mixing cell. The other one of these liquid compartments contained component B (calcium chloride was dissolved in various concentrations of acetic acid in order to adjust the pH of the activator solution). For samples containing hydroxyapatite crystals (HA; $Ca_5(PO_4)_3$OH; TRI-CAFOS PF, Budenheim; mean particle size: 5.0 μm; specific surface area of 70.1 $m^2/g$) the two powder components were mixed together in advance. Immediately after placing the mixing cell thus containing both components A and B within the calorimeter, the liquid component, i.e. the $MgCl_2$ solution, of component A was injected into the α-TCP powder and the powder and liquid were mixed together to a cement paste using the mixing rod present in the mixing cell. Following a 2 h incubation time during which both components reached the temperature of 37° C. as indicated by a constant calorimetric signal, component B was injected into the mixing cell containing component A and the formed paste was mixed with the mixing rod. The calorimetric signal was measured until a constant null value was obtained, typically more than 48 h after the injection of component B.

Addition of acetic acid into component B (samples 5-8) resulted in an initial setting reaction during the first few minutes after the injection of component B into the cement paste as illustrated in FIG. 4. This initial setting reaction caused by the slight acidity of component B was followed by the main cement reaction indicated by the slower release of heat occurring 1-40 h after the addition of component B into the cement paste as shown in FIG. 5. The setting reaction was further accelerated by the addition of HA seed crystals (sample 9). This acceleration of the hydraulic setting reaction was also detected in sample 10 containing no acetic acid. However, the total cumulated amount of released heat was somewhat lower for samples containing high concentration of acetic acid, seed crystals, or the combination of both as shown in FIG. 6.

Preferably the seed crystals should be contained in component B and mixed with component A only upon the eventual application of the cement paste. However, the HA crystals were added to the component A in the present example (samples 9 and 10) due to the narrow diameter of the inbuilt injection system of the mixing cells used in the calorimeter. Nonetheless, this was not considered to cause significant difference with the detected heat release rate because of the relatively short incubation time prior to the addition of component B to component A comprising the HA seed crystals.

EXAMPLE 4

Several cement samples with various compositions according to the invention were tested in an isothermal calorimeter at 37° C. using the parameters described in Table 1.

TABLE 3

Composition of the cement samples tested in isothermal calorimeter

| Sample | Component A | Component B |
|---|---|---|
| 11 | 2.0 g of calcined α-TCP powder | 1.0 ml demineralised $H_2O$ |
| 12 | 2.0 g of calcined α-TCP powder mixed with 0.8 ml 0.1M $SrCl_2$ solution | 0.2 ml 0.4M of $CaCl_2$ solution |
| 13 | 2.0 g of calcined α-TCP powder mixed with 0.8 ml 0.1M $SrCl_2$ solution | 0.2 ml 2.0M of $CaCl_2$ solution |
| 14 | 2.0 g of calcined α-TCP powder mixed with 0.8 ml 0.1M $SrCl_2$ solution | 0.2 ml 4.0M of $CaCl_2$ solution |
| 15 | 2.0 g of calcined α-TCP powder mixed with 1.0 ml 0.1M $SrCl_2$ solution | — |

The α-TCP powder (the same powder as used in Example 1) was placed in a glass vial compartment of the sealed mixing cell used for the calorimeter experiment, while the liquid component of A was placed in one of the two sealed injection compartments of the mixing cell. The other one of these liquid compartments contained component B. Immediately after placing the mixing cell thus containing both components A and B within the calorimeter, the liquid component, i.e. the $SrCl_2$ solution, of component A was injected into the α-TCP powder and the powder and liquid were mixed together to a cement paste using the mixing rod present in the mixing cell. Following a 2 h incubation time during which both components reached the temperature of 37° C. as indicated by a constant calorimetric signal, component B was injected into the mixing cell containing component A and the formed paste was mixed with the mixing rod. The calorimetric signal was measured until a constant null value was obtained, typically more than 48 h after the injection of component B.

The inhibitory effect of $Sr^{2+}$ ions on the setting reaction was found to be similar to the effect of $Mg^{2+}$ as presented in Example 2. No hydraulic cement reaction indicated by significant heat release was detected for the sample containing 0.1 M $SrCl_2$ solution during a 7 days testing period (Sample 15). In comparison, calcined α-TCP containing no $Sr^{2+}$ ions as nucleation and grain growth inhibitors (sample 11) reacted readily in aqueous environment with the setting reaction initiating less than 10 h after exposure to water (FIG. 7).

Similar to Example 2, the addition of increasing amount $Ca^{2+}$ ions as activators into component B (samples 12-14) resulted in increasingly accelerated initiation of the setting reaction with the highest tested concentration resulting in a hydraulic reaction after approximately 12 h as illustrated in FIG. 7. However, with $Ca^{2+}$-to-$Sr^{2+}$ ratios lower than 5:1, the reversal of the reaction inhibition with $Ca^{2+}$ ions appeared somewhat hampered as indicated by the altered heat release kinetics for sample 12 in comparison to sample 2 with corresponding $Ca^{2+}$-to-$Mg^{2+}$ ratio, whereas the total amount of heat released was no significantly affected (FIG. 8 vs. FIG. 3). Nonetheless, the total amount of heat released during the setting reaction was somewhat lower at low $Ca^{2+}$-to-$Sr^{2+}$ ratio, as was also shown to be the case with $Mg^{2+}$-stabilized α-TCP. These results indicate that, similar to $Mg^{2+}$ ions, $Sr^{2+}$ ions have a reversible inhibitory effect on the hydrolysis reaction of α-TCP as the added $Ca^{2+}$ ions have the capacity to displace the reaction inhibiting $Sr^{2+}$ ions on the α-TCP particle surface, thus initiating the cement reaction.

EXAMPLE 5

Several cement samples with various compositions according to the invention were tested in an isothermal calorimeter at 37° C. using the parameters described in Table 3.

TABLE 3

Composition of the cement samples tested in isothermal calorimeter

| Sample | Component A | Component B |
|---|---|---|
| 16 | 2.0 g of calcined α-TCP powder | 1.0 ml demineralised $H_2O$ |
| 17 | 2.0 g of calcined α-TCP powder mixed with 0.8 ml 0.01M $BaCl_2$ solution | 0.2 ml 0.4M of $CaCl_2$ solution |
| 18 | 2.0 g of calcined α-TCP powder mixed with 0.8 ml 0.05M $BaCl_2$ solution | 0.2 ml 2.0M of $CaCl_2$ solution |
| 19 | 2.0 g of calcined α-TCP powder mixed with 0.8 ml 0.1M $BaCl_2$ solution | 0.2 ml 4.0M of $CaCl_2$ solution |
| 20 | 2.0 g of calcined α-TCP powder mixed with 1.0 ml 0.01M $BaCl_2$ solution | — |

The α-TCP powder (the same powder as used in Example 1) was placed in a glass vial compartment of the sealed mixing cell used for the calorimeter experiment, while the liquid component of A was placed in one of the two sealed injection compartments of the mixing cell. The other one of these liquid compartments contained component B. Immediately after placing the mixing cell thus containing both components A and B within the calorimeter, the liquid component, i.e. the $BaCl_2$ solution, of component A was injected into the α-TCP powder and the powder and liquid were mixed together to a cement paste using the mixing rod present in the mixing cell. Following a 2 h incubation time during which both components reached the temperature of 37° C. as indicated by a constant calorimetric signal, component B was injected into the mixing cell containing component A and the formed paste was mixed with the mixing rod. The calorimetric signal was measured until a constant null value was obtained, typically more than 48 h after the injection of component B.

$Ba^{2+}$ ions were found to elicit a more potent inhibitory effect on the setting reaction of α-TCP cement in comparison to that induced by $Mg^{2+}$ and $Sr^{2+}$ ions (Examples 2 and 4). This was manifested by the capacity of $BaCl_2$ concentration as low as 0.01 M to fully repress the conversion of α-TCP to hydroxyapatite in aqueous environment throughout a 4 days testing period (sample 20). In comparison, calcined α-TCP containing no $Ba^{2+}$ ions as nucleation and grain growth inhibitors (sample 16) reacted readily in aqueous environment with the setting reaction initiating less than 10 h after exposure to water (FIGS. 9 and 10).

Similar to Examples 2 and 4, the addition of the component B, which contained $Ca^{2+}$ ions in $Ca^{2+}$-to-$Ba^{2+}$ ratio of 10:1, to the cement paste resulted in the initiation of the hydraulic setting reaction in samples 17 and 18 with initial $Ba^{2+}$ concentrations of 0.01 M and 0.05 M, respectively. These results indicate that, similar to $Mg^{2+}$ and $Sr^{2+}$ ions, $Ba^{2+}$ ions have a reversible inhibitory effect on the hydrolysis reaction of α-TCP as the added $Ca^{2+}$ ions have the capacity to displace the reaction inhibiting $Ba^{2+}$ ions on the α-TCP particle surface, thus initiating the cement reaction. However, unlike in the case of $Mg^{2+}$ and $Sr^{2+}$ ions, this inhibitory effect is only reversible at low $Ba^{2+}$ concentrations (<0.1 M) as no hydraulic reaction could be initiated at $BaCl_2$ concentration of 0.1 M by the addition of $Ca^{2+}$ ions at $Ca^{2+}$-to-$Ba^{2+}$ molar ratio of 10:1 (sample 19).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is appreciated that certain features of the invention, which are, for clarity, described in the context of separate embodiments, may also be provided in combination in a single embodiment. Conversely, various features of the invention, which, for brevity, are described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

The invention claimed is:

1. A precursor to a calcium phosphate cement composition, said precursor comprising two distinct components A and B that are kept separate from each other:
   wherein component A comprises one or more calcium phosphate powders suspended in an aqueous solution that includes inhibitor cations inhibiting a reaction of the calcium phosphate powders with water, the inhibitor cations being selected from the group consisting of $Mg^{2+}$, $Sr^{2+}$ and $Ba^{2+}$ and being present in the aqueous solution of component A at a concentration greater than 0.01 M;
   wherein component B comprises a second aqueous solution comprising $Ca^{2+}$ cations at a concentration greater than 0.1 M; and
   wherein a ratio of an amount of component A to component B is such that upon mixing components A and B together to form a mixture, a molar ratio of $Ca^{2+}$ ions to inhibitor cations in the mixture is greater than 2.

2. The precursor according to claim 1, wherein the inhibitor cations are $Mg^{2+}$ only.

3. The precursor according to claim 1, wherein the inhibitor cations are $Sr^{2+}$ only.

4. The precursor according to claim 1, wherein the ratio of the amount of component A to component B is such that upon mixing components A and B together to form the mixture, the molar ratio of $Ca^{2+}$ ions to inhibitor cations in the mixture is greater than 5.

5. The precursor according to claim 1, wherein the calcium phosphate powder is alpha-tricalcium phosphate.

6. The precursor according to claim 1, wherein the calcium phosphate powder is amorphous calcium phosphate.

7. The precursor according to claim 1, wherein the calcium phosphate powder is obtained by calcination at a temperature in a range of 400° C. to 700° C. for at least 10 minutes.

8. The precursor according to claim 1, wherein the molar concentration of the inhibitor cations in the aqueous solution of component A is equal to or greater than 0.05 M.

9. The precursor according to claim 1, wherein component B comprises calcium salts having a solubility greater than 0.5 M.

10. The precursor according to claim 1, wherein component B comprises one or more calcium salts selected from the group consisting of anhydrous calcium chloride, calcium chloride monohydrate, calcium chloride dihydrate, calcium chloride hexahydrate, dicalcium phosphate dihydrate, calcium sulphate dihydrate, calcium sulfate hemihydrate, calcium sulfate, calcium nitrate, anhydrous calcium acetate, calcium acetate monohydrate, calcium acetate dihydrate, calcium citrate, calcium fumarate, calcium glycerophosphate, calcium lactate, calcium dl-malate, calcium l-malate, calcium malate dihydrogen, calcium maleate, calcium malonate, calcium oxalate, calcium oxalate hydrate, calcium salicylate, calcium succinate, calcium d-tartrate, calcium dl-tartrate, calcium mesotartrate, and calcium valerate.

11. The precursor according to claim 1, wherein a volume ratio of component A to component B is equal to or larger than 4.

12. The precursor according to claim 1, wherein a volume ratio of component A to component B is lower than 12.

13. The precursor according to claim 1, wherein the concentration of Ca2+ ions in component B is greater than to 0.5 M.

14. The precursor according to claim 1, wherein the component B further comprises a calcium phosphate powder.

15. The precursor according to claim 14, wherein the calcium phosphate powder in component B comprises an apatite.

16. The precursor according to claim 14, wherein the quantity of calcium phosphate powder in component B is equal to or greater than 0.4 g/mL.

17. The precursor according to claim 14, wherein the calcium phosphate powder in component B is in the form of nanocrystals.

18. The precursor according to claim 1, wherein component A or component B or both component A and component B comprise a small amount of water soluble polymer.

19. The precursor according to claim 18, wherein the polymer is selected from the group consisting of: (i) hyaluronan; (ii) chondroitin sulfate; (iii) cellulose derivatives; (iv) polyvinylpyrrolidone; (v) N-methyl-2-pyrrolydone; (vi) dimethylsiloxane; (vii) alginate; (viii) chitosan; (ix) gelatin; and (x) collagen.

20. The precursor according to claim 18, wherein the polymer is present in an amount of at least 0.1 weight percent.

21. The precursor according to claim 18, wherein the polymer is present in an amount no greater than 3.0 weight percent.

22. The precursor according to claim 1, further comprising a radiopacifier selected from the the group consisting of: (i) iodine based solutions; (ii) metallic powders and (iii) ceramics.

23. The precursor according to claim 1, wherein a calcium phosphate-to-liquid weight ratio, upon mixing of components A and B, is equal to or greater than 2.

24. The precursor according to claim 1, wherein component B has a pH equal to or lower than 6.

25. The precursor according to claim 24, wherein the pH of component B is adjusted using a weak acid.

26. The precursor according to claim 25, wherein the weak acid in component B is present at a concentration equal to or greater than 0.1 M.

27. The precursor according to claim 1, wherein component A has a pH greater than 8.

28. The precursor according to claim 5, wherein the alpha-tricalcium phosphate has a purity of greater than 80%.

29. The precursor according to claim 28, wherein the alpha-tricalcium phosphate is contaminated with apatite.

30. The precursor according to claim 5, wherein the alpha-tricalcium phosphate has a specific surface area (SSA) greater than 0.5 m2/g.

* * * * *